United States Patent
Shekhar et al.

(10) Patent No.: US 6,740,776 B2
(45) Date of Patent: May 25, 2004

(54) AIR OXIDATION OF AN AROMATIC ALDEHYDE TO AN AROMATIC ACID

(75) Inventors: Ratna Shekhar, Madison, NJ (US); Michael John Girgis, Montville, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/196,600

(22) Filed: Jul. 15, 2002

(65) Prior Publication Data

US 2003/0023115 A1 Jan. 30, 2003

Related U.S. Application Data

(60) Provisional application No. 60/305,648, filed on Jul. 16, 2001.

(51) Int. Cl.[7] ............................................. C07C 51/23
(52) U.S. Cl. ..................................... 562/418; 562/421
(58) Field of Search ................................. 562/418, 421

(56) References Cited

U.S. PATENT DOCUMENTS

| | | | |
|---|---|---|---|
| 3,775,472 A | * 11/1973 | Massie | 260/524 |
| 3,946,067 A | 3/1976 | Kwiatek et al. | 260/476 |

(List continued on next page.)

FOREIGN PATENT DOCUMENTS

| | | | |
|---|---|---|---|
| GB | 644667 | | 10/1950 |
| GB | 1 282 775 | | 7/1972 |
| JP | 03038100 | | 5/2000 |
| JP | 2001-131113 | * | 5/2001 |

OTHER PUBLICATIONS

George et al, "Direct liquid–phase side–chain oxidation of alkylbenzenes over [Pd(phen)(OAc)2] catalyst" Catalysis Letters, vol. 65, pp. 181–183 (2000).*

(List continued on next page.)

Primary Examiner—Richard L. Raymond
Assistant Examiner—Zachary C. Tucker
(74) Attorney, Agent, or Firm—Paivi Kukkola; John D. Thallemer

(57) ABSTRACT

A low temperature process for preparing an aromatic acid having formula (I),

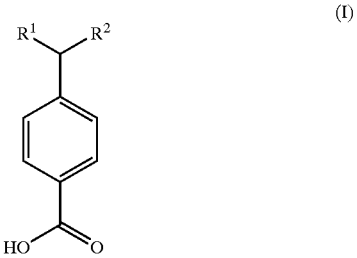

(I)

said process comprising reacting an aromatic aldehyde having formula (II)

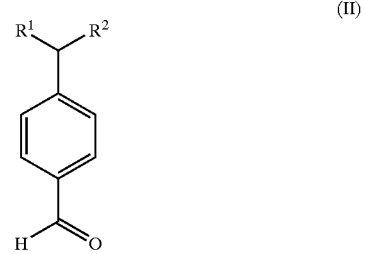

(II)

with a gas having an oxygen content of 1 to 100 weight percent, based on the total weight of the gas, at a temperature of about 20° C. to less than 100° C. in the presence of a supported Group VIII metal catalyst, and a solvent having a flash point greater than 95° C. and/or a melting point less than 55° C., provided that the flash point of the solvent is greater than the reaction temperature, wherein $R^1$ and $R^2$ are independently selected from the group consisting of hydrogen and a $C_1$–$C_8$ linear, branched or cyclic alkyl group. The process of the invention yields an aromatic acid in excellent yield, and (i) does not involve the use of deleterious oxidizing agents; (ii) is essentially free of by-products; and (iii) is accomplished at a temperature of less than 100° C.

18 Claims, 2 Drawing Sheets

(a) IBA Conversion (%) and Cumic Acid Yield (%)

U.S. PATENT DOCUMENTS

| | | |
|---|---|---|
| 4,097,533 A | 6/1978 | Scheben ................... 260/599 |
| 4,603,220 A | 7/1986 | Feld ......................... 562/416 |
| 4,816,484 A | 3/1989 | Toyoshima et al. ......... 514/563 |
| 5,110,982 A | 5/1992 | Tanaka et al. .............. 562/414 |
| 5,189,209 A | 2/1993 | Ohta et al. .................. 562/414 |
| 5,684,187 A | 11/1997 | Ohkoshi et al. ............ 562/486 |
| 5,686,638 A | 11/1997 | Kos et al. ................... 554/134 |
| 5,693,856 A | 12/1997 | Ramachandran et al. ... 562/414 |
| 5,705,682 A | 1/1998 | Ohkoshi et al. ............ 562/414 |
| 6,022,899 A | 2/2000 | Kleemann et al. .......... 514/595 |
| 6,218,431 B1 | 4/2001 | Schoen et al. .............. 514/520 |

OTHER PUBLICATIONS

Mukhopadhyay, Organic Process Research & Development, "Kinetics and Process Parameter Studies in Catalytic Air Oxidation of Veratraldehyde to Veratric Acid", vol. 3, No. 5, pp. 365–369 (1999).

Miyagawa et al, Chemical Abstracts 111:7066, 1989:407066 (JP 63264551—Nov. 1, 1988).

\* cited by examiner

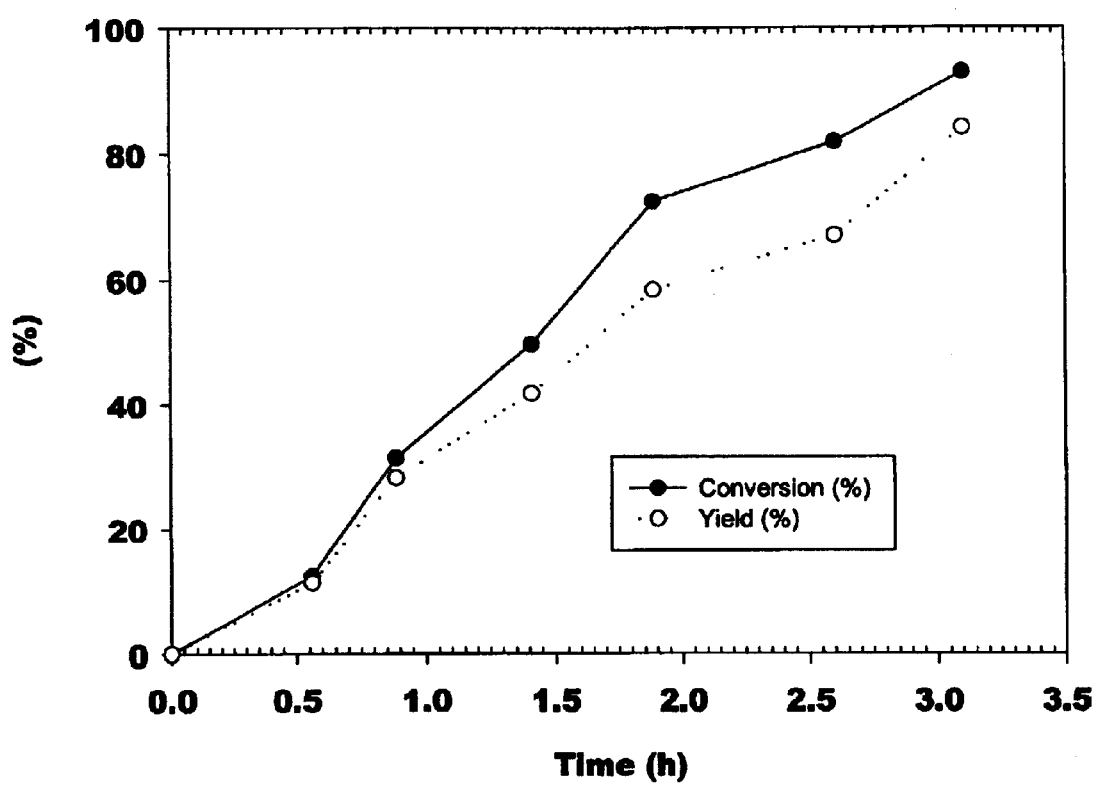
Figure 1:(a) IBA Conversion (%) and Cumic Acid Yield (%)

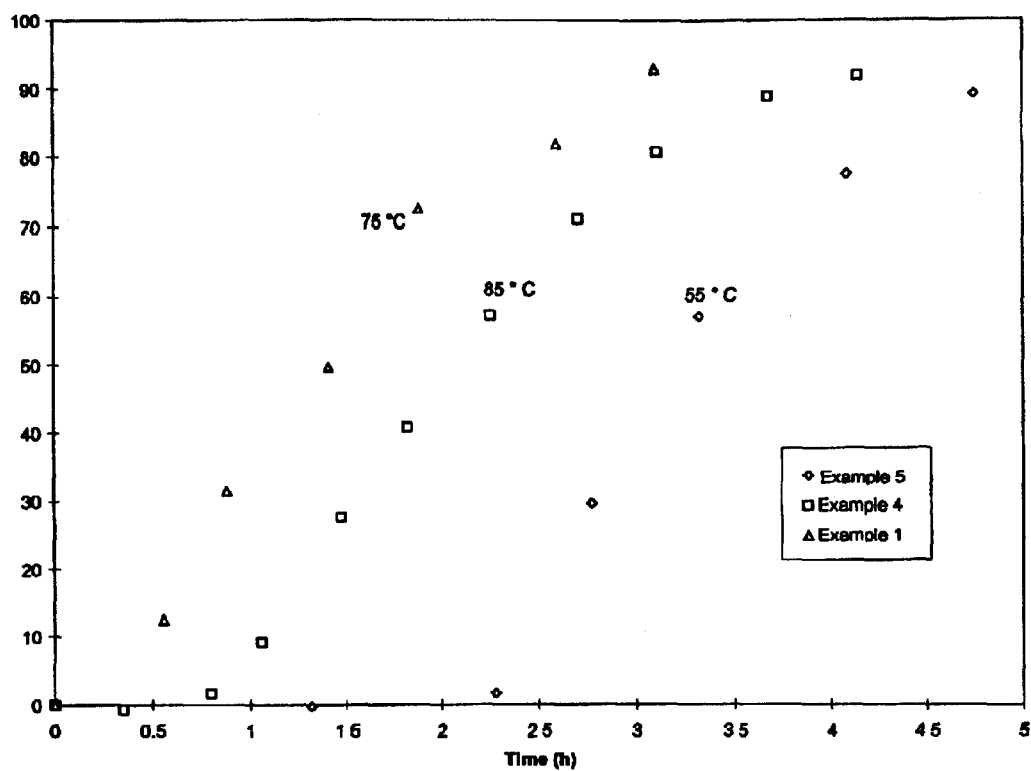
Figure 2: Effect of process temperature on conversion for Examples 1, 4, and 5.

AIR OXIDATION OF AN AROMATIC ALDEHYDE TO AN AROMATIC ACID

This application claims benefit to U.S. Provisional Application No. 60/305,648, filed Jul. 16, 2001.

FIELD OF THE INVENTION

The present invention provides a low temperature process for preparing an aromatic acid by reacting an aromatic aldehyde with air at a temperature of about 20° C. to less than 100° C. in the presence of a supported Group VIII metal catalyst.

BACKGROUND OF THE INVENTION

4-Isopropylbenzoic acid (cumic acid or cuminic acid), which is an aromatic mono-carboxylic acid, is an important organic intermediate in the production of pharmaceutical compounds. For example, 4-isopropylbenzoic acid can be used to synthesize nateglinide, a compound for treating diabetes available under the trademark STARLIX from Novartis. Several methods have been used to prepare isopropylbenzoic acid from isopropylbenzaldehyde. Such methods typically employ deleterious oxidizing agents, such as peroxides, NaOCl, peracids, $NaIO_4$, and $O_3$ which can be used with or without a catalyst. The use of such oxidizing agents, however, pose safety concerns because they are corrosive, and disposing of such oxidizing agents may cause environmental problems, especially the by-product salts such as halogen-containing oxidants.

U.S. Pat. No. 3,946,067 describes a process for preparing benzaldehyde by vapor phase oxidation of toluene at a temperature from 100° C. to 250° C. in the presence of a catalyst composition containing phosphoric acid and a palladium metal. U.S. Pat. No. 5,693,856 describes a process for preparing terephthalic acid which involves reacting a polyalkyl benzene compound with oxygen in the presence of a heavy metal catalyst at a temperature from 150° C. to 250° C. U.S. Pat. No. 5,686,638 describes a process for preparing mono- or dicarboxylic acids from an aldehyde without using a catalyst or an aprotic solvent, which involves oxidizing the aldehyde in a carboxylic acid as diluent or carboxylic acid/water mixture.

U.S. Pat. No. 5,189,209 describes a process for preparing highly pure isophthalic acid which involves oxidizing m-dialkyl benzene with molecular oxygen in an acetic acid solvent in the presence of a heavy metal catalyst at a temperature of 100° C. to 240° C. to form crude isophthalic acid; and contacting the crude isophthalic acid with a Group VIII catalyst supported by activated carbon in the presence of hydrogen at a temperature of 170° C. to 300° C. U.S. Pat. No. 5,110,982 describes a process for producing 2,6-naphthalene dicarboxylic acid which involves oxidizing a 2-alkyl-6-acyl naphthalene with molecular oxygen-containing gas in the presence of a catalyst containing cobalt, manganese, and bromine in an acetic acid solvent. U.S. Pat. No. 4,603,220 describes a process for preparing aromatic monocarboxylic acids by oxidation of a liquid phase of toluene or substituted toluenes with oxygen or gas containing oxygen, and a heavy metal catalyst.

Japanese Patent No. 3038100 describes a process for preparing aromatic carboxylic acids by oxidation of aromatic aldehydes with a peracid. Japanese Patent Application No. 87-99169 describes preparing cuminic acid by oxidation of cuminaldehyde with hydrogen peroxide under alkaline conditions.

Air oxidation of 3,4-dimethoxybenzaldehyde to 3,4-dimethoxybenzoic acid using cobalt acetate, manganese acetate, or lithium bromide as catalysts and a reaction temperature of from 110° C. to 140° C. is described by Mukhopadhyay, *Organic Process Research & Development*, Vol. 3, pp. 365–369 (1999).

Therefore, it is desirable from a safety and environmental standpoint to develop a process for preparing an aromatic acid from an aromatic aldehyde that (i) does not involve the use of deleterious oxidizing agents; (ii) is essentially free of by-products; and (iii) is accomplished at a temperature of less than 100° C.

SUMMARY OF THE INVENTION

The invention provides a low temperature process for preparing an aromatic acid having formula (I),

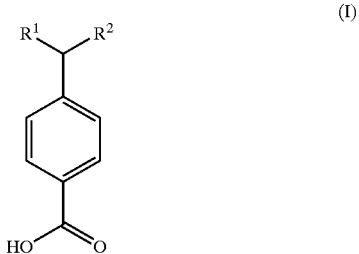

said process comprising reacting an aromatic aldehyde having formula (II)

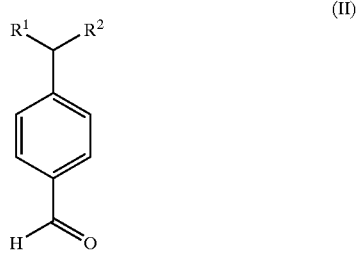

with a gas having an oxygen content of 1 to 100 weight percent, based on the total weight of the gas, at a temperature of about 20° C. to less than 100° C. in the presence of a supported Group VIII metal catalyst, and a solvent having a flash point greater than 95° C. and/or a melting point less than 55° C., provided that the flash point of the solvent is greater than the reaction temperature, wherein $R^1$ and $R^2$ are independently selected from the group consisting of hydrogen and a $C_1$–$C_8$ linear, branched or cyclic alkyl group. Preferably the aromatic acid is 4-isopropylbenzoic acid and the aromatic aldehyde is 4-isopropylbenzaldehyde.

The process of the invention yields an aromatic acid in excellent yield, and (i) does not involve the use of deleterious oxidizing agents such as peroxides, NaOCl, peracids, $NaIO_4$, and $O_3$; (ii) is essentially free of by-products; and (iii) is accomplished at a temperature of less than 100° C.

BRIEF DESCRIPTION OF THE DRAWINGS

FIG. 1 is a graph of 4-isopropylbenzaldehyde conversion and 4-isopropylbenzoic acid yield vs. time.

FIG. 2 is a graph of 4-isopropylbenzaldehyde conversion vs. time at three different temperatures.

DESCRIPTION OF THE INVENTION

The process of the invention is used to prepare an aromatic acid having formula (I),

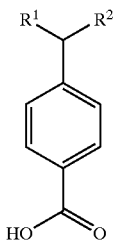

(I)

wherein R¹ and R² are independently selected from the group consisting of hydrogen and a $C_1$–$C_8$ linear, branched or cyclic alkyl group. The process involves reacting an aromatic aldehyde having formula (II)

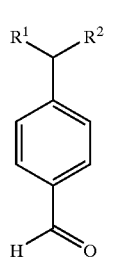

(II)

with a gas having an oxygen content of 1 to 100 weight percent, based on the total weight of the gas, at a temperature of about 20° C. to less than 100° C. in the presence of a supported Group VII metal catalyst and a solvent. In formula (II), R¹ and R² are independently selected from the group consisting of hydrogen and a $C_1$–$C_8$ linear, branched or cyclic alkyl group. Preferably R¹ and R² are $CH_3$. Preferably the aromatic acid is 4-isopropylbenzoic acid and the aromatic aldehyde is 4-isopropylbenzaldehyde.

The process is conducted in the presence of a gas having an oxygen content of from 1 to 100 weight percent, based on the total weight of the gas. Preferably, the oxygen content of the gas is from about 20 to about 50 weight percent, more preferably, from about 21 to about 25 weight percent. Most preferably, the gas is air having an oxygen content of about 23 weight percent.

The catalyst used in the process of the invention is a supported Group VIII metal catalyst. Examples of metals belonging to Group VIII of the Periodic Table include ruthenium, rhodium, palladium, osmium, iridium and platinum. A combination of metals may also be used. Preferably the metal is platinum. The support includes any conventional catalyst carrier, such as, for example, carbon, silica, alumina, titania, carborundum and ion-exchange resin. A combination of supports may also be used. Preferably the support is activated carbon. The support is impregnated or loaded with the Group VIII metal, or the Group VIII metal is deposited on the support.

The Group VIII metal is incorporated on the support in an amount of from 0.1 to 20 weight percent, based on the total weight of the metal and support. Preferably, the metal is incorporated in an amount of from 5 to 10 weight percent. Preferred catalysts for use in the process of the invention are Pt/C and Pt/$Al_2O_3$. A combination of catalysts may also be used. It is within the scope of the invention that the catalyst may also include a promoter or co-promoter.

In one embodiment of the invention, a heterogeneous catalyst is used in order to facilitate catalyst separation and recovery of the aromatic acid product.

The reaction is preferably conducted at a temperature of from about 20° C. to less than 100° C., more preferably, 55° C. to 85° C.; and under a pressure of from about 1 atm to about 200 atm, more preferably, 50 atm to 100 atm. Most preferably, the reaction is conducted at a temperature of about 75° C. at 1 atm.

The process of the invention is conducted in the presence of at least one solvent having a flash point greater than 95° C. and/or a melting point less than 55° C. As used herein, "flash point" means the temperature at which a liquid or volatile solid gives off vapor sufficient to form an ignitable mixture with the air near the surface of the liquid or within the reaction vessel. The flash point may be determined by the Tagliabue open cup method (ASTM D1310-63). Additional methods for determining the flash point are the Tagliabue closed cup method and the Cleveland open cup method. The flash point of the solvent must be greater than the temperature at which the reaction is conducted. Preferably, the flash point of the solvent is significantly greater than the temperature of the reaction. As used herein, "significantly greater" means that the flash point of the solvent is at least 10° C. greater than the reaction temperature.

Suitable solvents include $C_{14}$ to $C_{24}$ parraffins, such as tetradecane (f.p 99° C., m.p. <20° C.), hexadecane (f.p 135° C., m.p. <20° C.), octadecane (f.p 165° C., m.p. 28–30° C.), eicosane (f.p>110° C., m.p. 36–38° C.) and tetraeicosane (f.p>110° C., m.p. <49–52° C.). In addition, suitable solvents include mineral oil, dimethyl siloxane, dimethicone and petrolatum. A combination of solvents may also be used. Preferably, the solvent is inert to oxidation under the reaction conditions. A preferred solvent is mineral oil.

The catalyst is separated from the reaction mixture by filtration. The aromatic acid product is separated by any convenient means such as distillation and/or extraction. Unreacted feed material separated from the recovered effluent may be recycled for further reaction.

Referring to FIG. 1, a graph of 4-isopropylbenzaldehyde conversion and 4-isopropylbenzoic acid yield vs. time is depicted. The yield was determined by gas chromatography peak area normalization. FIG. 1 clearly shows that the 4-isopropylbenzaldehyde conversion and 4-isopropylbenzoic acid yield increase to about 90% after 3 hours.

Referring to FIG. 2, a graph of 4-isopropylbenzaldehyde conversion vs. time at three different temperatures is depicted. FIG. 2 clearly shows that the length of the induction period changed significantly with temperature, decreasing almost six-fold as the temperature increased from 55° C. to 75° C.

The following non-limiting examples illustrate further aspects of the invention.

EXAMPLE 1

Preparation of 4-Isopropylbenzoic Acid

A 1 liter jacketed reaction vessel equipped with a temperature sensor and agitator was charged with 67 grams of isopropylbenzaldehyde (IBA), 13.4 grams of Pt/C catalyst, and 335.2 grams of light mineral oil. White mineral oil (d 0.838, Merck Index 11,7139, flash point>110° C.) was used as a solvent. The Pt/C catalyst was 5% Pt/C with ca. 60% moisture content.

With the agitator running, nitrogen gas was bubbled into the liquid mixture at 0.43 L/min L of solution. The reaction mixture was heated by the jacket to 75° C., at which time air was sparged into the reaction mixture. Technical grade supplies of nitrogen and instrument air were used. Both the nitrogen and air were introduced using a porous 2 p-opening SS filter element (Fisher Scientific), fitted on a ⅛-inch 316-SS tube. Gas flow into the reactor was regulated with a calibrated mass flow controller. The outgoing gas was passed through a chilled glass condenser kept outside the reactor.

Analytical analysis determined that approximately 94% cumic acid conversion was achieved in 6 hours, with cumic acid (98+%) used as GC standard. Conversion after 20 hours was 99.4%. The process variables and test results are summarized in Table I.

EXAMPLE 2
Preparation of 4-Isopropylbenzoic Acid

The procedure set forth in Example 1 was followed except that the catalyst concentration was reduced from 20 weight percent to 10 weight percent, based on the total weight of IBA. Conversion after 22 hours was 93%. The process variables and test results are summarized in Table I.

EXAMPLE 3
Preparation of 4-Isopropylbenzoic Acid

The procedure set forth in Example 1 was followed except that the catalyst concentration was reduced from 20 weight percent to 10 weight percent, based on the total weight of IBA, the amount of IBA was decreased from 23% to 19%, the catalyst was 5% Pt/Al$_2$O$_3$ with ca. 60% moisture content, and the agitation rate was increased from 300 rpm to 550 rpm. Conversion after 19 hours was 75%. The process variables and test results are summarized in Table I.

EXAMPLE 4
Preparation of 4-Isopropylbenzoic Acid

The procedure set forth in Example 1 was followed except that the reaction temperature was increased from 75° C. to 85° C. Conversion after 4.1 hours was 92%. The process variables and test results are summarized in Table I.

EXAMPLE 5
Preparation of 4-Isopropylbenzoic Acid

The procedure set forth in Example 1 was followed except that the catalyst concentration was increased from 20% to 24%, and the reaction temperature was decreased from 75° C. to 55° C. Conversion after 4.1 hours was 78%. The process variables and test results are summarized in Table I.

TABLE I

| Process Variable | Example 1 | Example 2 | Example 3 | Example 4 | Example 5 |
|---|---|---|---|---|---|
| IBA Conc. (g of IBA/g of Mixture) | 0.23 | 0.23 | 0.19 | 0.23 | 0.20 |
| Catalyst Conc. (g of Catalyst/g of IBA) | 0.20 | 0.10 | 0.10 | 0.20 | 0.24 |
| Catalyst Type | 5% Pt/C | 5% Pt/C | 5% Pt/Al$_2$O$_3$ | 5% Pt/C | 5% Pt/C |
| Air Sparging Rate (cm$^3$/min/cm$^3$ of Mixture) | 0.8 | 0.8 | 0.83 | 0.8 | 0.82 |
| Temperature (° C.) | 75 | 75 | 75 | 85 | 55 |
| Agitation Rate (rpm) | 300 | 300 | 550 | 300 | 300 |
| Conversion | 99.4 | 93 | 75 | 92 | 78 |
| Selectivity (%) | 75 | 77 | >70 | 84 | 98 |
| *Yield (%) | 74 | 71 | >70 | 77 | 76 |
| Reaction Time (hours) | 20 | 22 | 19 | 4.1 | 4.1 |

*Based on gas chromatography peak area normalization.

The results in Table I clearly show that the process of the invention produces 4-isopropylbenzoic acid in high yield.

Thus, the process of the invention yields an aromatic acid in excellent yield, and (i) does not involve the use of deleterious oxidizing agents such as peroxides, NaOCl, peracids, NaIO$_4$ and O$_3$; (ii) is essentially free of by-products; and (iii) is accomplished at a temperature of less than 100° C.

While the invention has been described with particular reference to certain embodiments thereof, it will be understood that changes and modifications may be made by those of ordinary skill within the scope and spirit of the following claims:

What is claimed is:

1. A low temperature process for preparing an aromatic acid having formula (I),

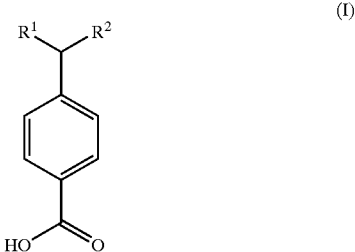

(I)

said process comprising reacting an aromatic aldehyde having formula (II)

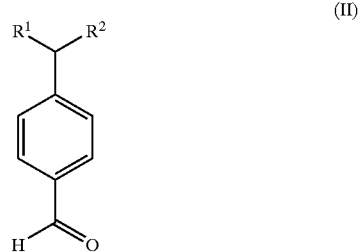

(II)

with a gas having an oxygen content of 1 to 100 weight percent, based on the total weight of the gas, at a temperature of about 20° C. to less than 100° C. in the presence of a supported Group VIII metal catalyst, and a solvent having a flash point greater than 95° C. and/or a melting point less than 55° C., provided that the flash point of the solvent is greater than the reaction temperature,
wherein R$^1$ and R$^2$ are independently selected from the group consisting of hydrogen and a C$_1$–C$_8$ linear, branched or cyclic alkyl group.

2. The process according to claim 1 wherein the aromatic acid is 4-isopropylbenzoic acid.

3. The process according to claim 1 wherein the Group VIII metal is selected from the group consisting of ruthenium, rhodium, palladium, osmium, iridium, platinum and combinations thereof.

4. The process according to claim 3 wherein the Group VIII metal is platinum.

5. The process according to claim 1 wherein the catalyst support is selected from the group consisting of carbon, silica, alumina, titania, carborundum, an ion-exchange resin and combinations thereof.

6. The process according to claim 5 wherein the catalyst support is activated carbon.

7. The process according to claim 1 wherein the supported catalyst is selected from the group consisting of Pt/IC and Pt/Al$_2$O$_3$.

8. The process according to claim 1 wherein the Group VIII metal is Incorporated on the support in an amount of from 0.1 to 20 weight percent, based on the total weight of the metal and support.

9. The process according to claim 8 wherein the Group VIII metal is incorporated on the support in an amount of from 5 to 10 weight percent.

10. The process according to claim 1 wherein the temperature is from about 55° C. to about 85° C.

11. The process according to claim 10 wherein the temperature is from about 70° C. to about 80° C.

12. The process according to claim 11 wherein the temperature is about 75° C.

13. The process according to claim 1 wherein the gas has an oxygen content of about 20 to about 50 weight percent.

14. The process according claim 13 wherein the gas has an oxygen content of about 21 to about 25 weight percent.

15. The process according to claim 14 wherein the gas is air having an oxygen content of about 23 weight percent.

16. The process according to claim 1 wherein the solvent is selected from the group consisting of $C_{14}$ to $C_{24}$ parraffins, mineral oil, dimethyl siloxane, dimethicone, petrolatum and combinations thereof.

17. The process according to claim 16 wherein the solvent is selected from the group consisting of tetradecane, hexadecane, octadecane, eicosane and tetraeicosane.

18. The process according to claim 17 wherein the solvent is mineral oil.

* * * * *